United States Patent [19]

Usukura

[11] 4,323,061
[45] Apr. 6, 1982

[54] STIFF SUPPORTING BANDAGE

[75] Inventor: Koji Usukura, Saitama, Japan

[73] Assignee: Tokyo Eizai Laboratory Co., Ltd., Tokyo, Japan

[21] Appl. No.: 80,041

[22] Filed: Sep. 28, 1979

[30] Foreign Application Priority Data

Oct. 4, 1978 [JP] Japan .................................. 53-122339

[51] Int. Cl.³ .............................................. A61F 5/04
[52] U.S. Cl. ...................................... 128/90; 128/156
[58] Field of Search ............... 128/90 R, 156; 66/195, 66/202

[56] References Cited

U.S. PATENT DOCUMENTS 3,618,599 11/1971 Beightol .................................. 128/90
3,882,857 5/1975 Woodall .................................. 128/90
4,108,169 8/1978 Parker .................................... 128/90

OTHER PUBLICATIONS

"Glass Plastic Cast", Amer. J. Surgery, Anderson et al., Sep. 1945, pp. 299-305.

Primary Examiner—Robert W. Michell
Assistant Examiner—T. J. Wallen
Attorney, Agent, or Firm—Hill, Van Santen, Steadman, Chiara & Simpson

[57] ABSTRACT

An improved two-part material for use in surgical bandages is formed of glass fibres combined with non-glass fibres.

1 Claim, 15 Drawing Figures

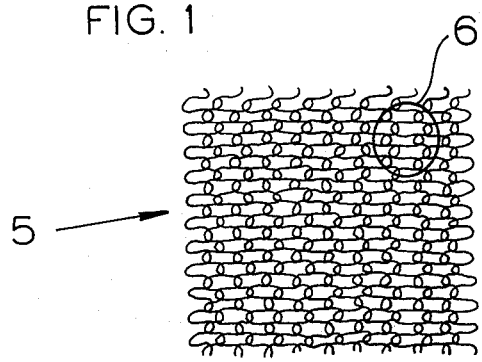
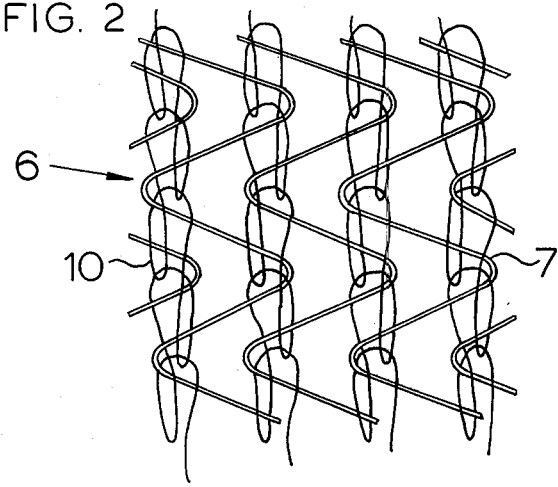
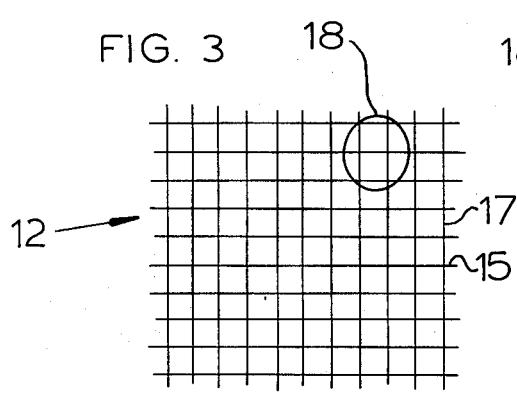
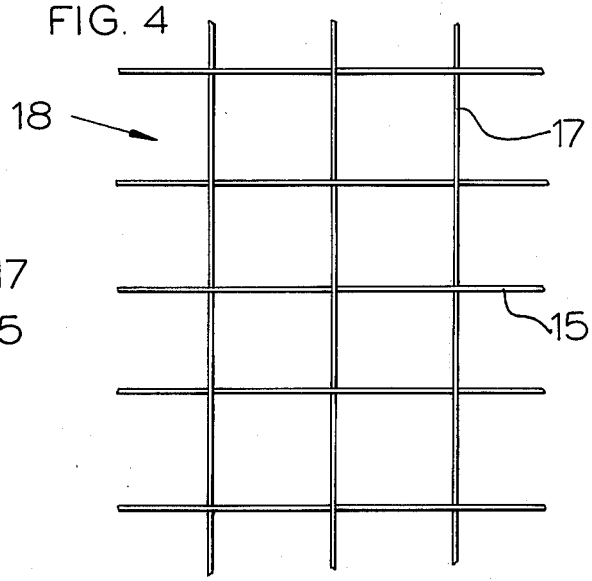
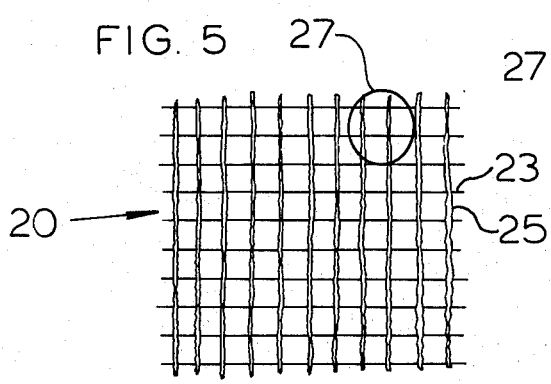
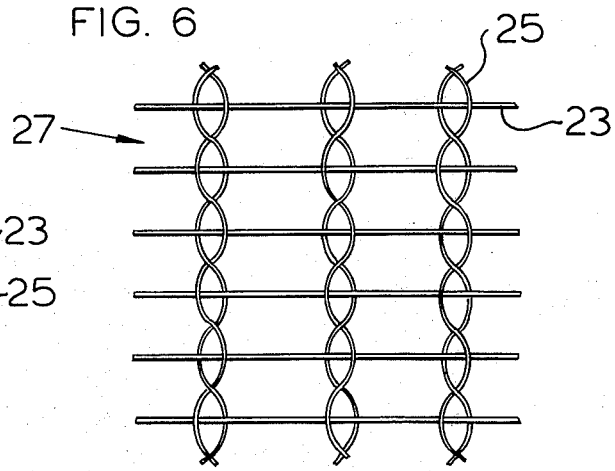

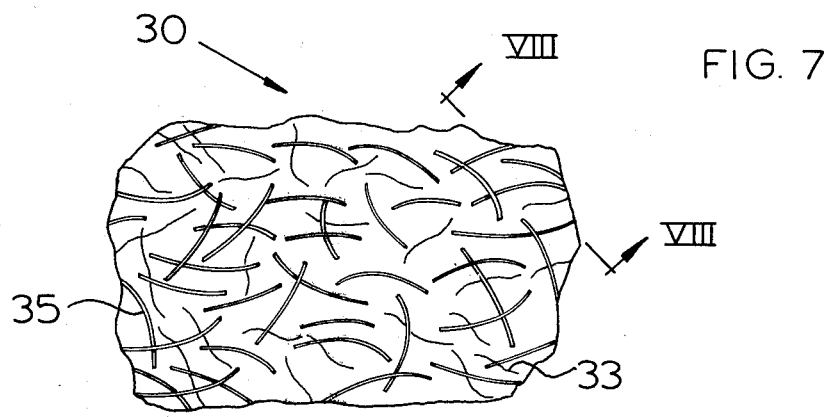
FIG. 7
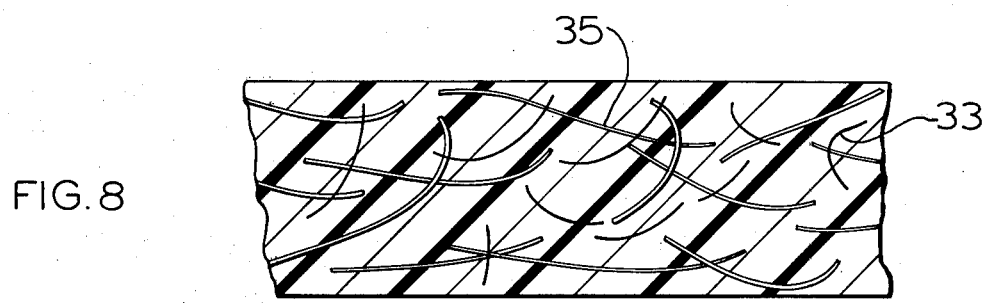
FIG. 8
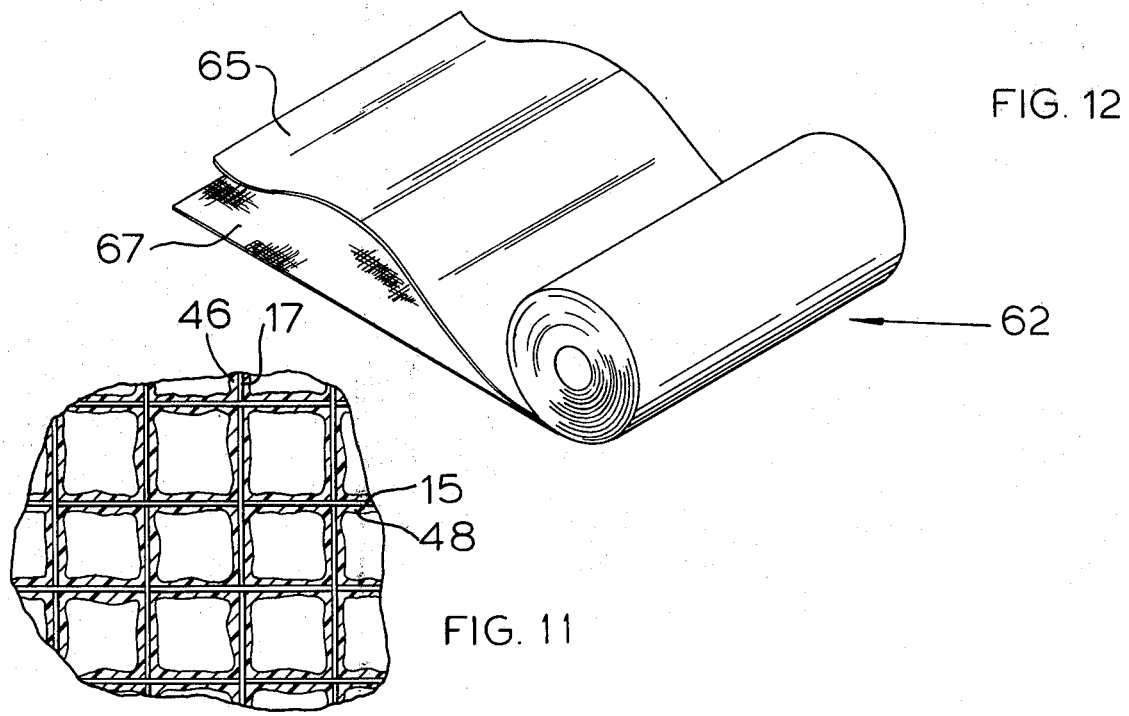
FIG. 12
FIG. 11

STIFF SUPPORTING BANDAGE

BACKGROUND OF THE INVENTION

1. Field of the Invention

This invention relates to a stiff supporting bandage, which is light in weight, high in rigidity and strength and which is suitable to cover, set, protect and re-form a damaged member including bone fractures, dislocations, sprains or deformations in humans as well as in animal bodies.

2. Prior Art

Stiff supporting bandages incorporating cloth and plaster of Paris are well known. The powder of plaster of Paris, dosed with a viscosity promoter, an endosmotic agent and a solidifying rate adjuster, is made into a powder, or into a suspension within an insoluble liquid. This compound is then coated onto or impregnated into cotton cloth or a basic fabric. The coated or impregnated fabric is then formed into a roll or a pile of sheets for general use. Stiff supporting bandages, wherein plaster of Paris is utilized as solidifiable material, are very high in rigidity, and are easily modeled to accommodate the damaged member or any irregularity thereof. Such bandages, however, have drawbacks. These include, weighing too much, being brittle, having poor permeability to X-rays and being easily stained.

Solidifiable resins which provide an alternate to plaster of Paris are available whose rigidity is sensitive to light, heat or catalytic agents. A suitable photo-solidifiable resin consists of unsaturated polyester and a sensitizer; suitable thermo-plastic resins include caprolactone, ethylene vinyl vinylchloride copolymer, and tran-stype polyisoprene. Suitable reactable resins consist of polyurethane resin and isocyanide, or polyacrylic acid and dimetallic salt. A solidifiable resin as disclosed above may be applied to a basic fabric consisting of woven or knitted cotton fibre or glass fibre. The treated fabric may then be formed into a roll or a pile of sheets. A stiff supporting bandage utilizing one of the above listed resins and a fabric formed of cotton or glass fibres is considerably improved in weight, stain resistance, ventilability, and X-ray permeability.

However, a fabric consisting of glass fibres alone has been found to be incapable of retaining a sufficient amount of solidifiable material. The surface smoothness of the glass fibres limits the amount of solidifiable material retainable by the fabric. Consequently, such a bandage would need to be wound in 8 to 10 layers to produce the necessary strength and rigidity. The added layers of bandage increase the cost, require excessive time to apply and are a great burden for the patient. Because of poor adhesiveness between the glass fibres and the solidifiable material it has been found that, if the protected portion suffers an impact after the solidifiable material has set, it could easily crack.

On the other hand, a basic fabric formed of cotton, flax, staple fibre, rayon, wool, acrylonitrile, nylon, polyester or the like, readily retains adequate solidifiable material. Bandages utilizing these fabrics have the disadvantages of an insufficient setting force and too high an elasticity. As a result, it is difficult to hold the damaged member precisely in a stiffened state. This limitation results in a very narrow range of application of these bandages. There has thus been an unfilled need for an improved fabric usable with the above identified resins and other solidifiable materials.

SUMMARY OF THE INVENTION

The inventor, after repeated practical tests, has found a unique material resulting in an improved, stiff, supporting bandage. The improved fabric is formed, in one embodiment, of a mixed yarn. The mixed yarn may be spun from glass fibre together with another fibre. The improved fabric may also be woven or knitted from yarns spun independently from glass fibre and another fibre. Alternately, the improved fabric may be formed as an unwoven cloth including glass fibre.

When a solidifiable material is applied to the improved fabric to make a bandage, the result is a bandage of sufficient rigidity, as well as strength, having the merits inherent to those of prior art, which is applicable to a much wider range of service.

The drawbacks of the prior art bandages are eliminated by the stiff supporting bandage according to this invention. The improved bandage is characterized in that the fabric material is a cloth having been woven, knitted or unwoven of glass fibres and one or more other fibres. The improved fabric is then coated, impregnated or adhered with a selected solidifiable material.

The improved fabric is one embodiment comprises woven, knitted or unwoven cloth of a glass fibre yarn and another yarn spun into a compound yarn of glass fibres and at least one fibre selected from cotton, flax, staple fibre, rayon, wool, acrylic resin, nylon, teflon, polyester and the like.

Alternately, the improved fabric may be woven, knitted or unwoven cloth comprising the glass fibre yarn and another yarn spun from at least one fibre out of cotton, flax, staple fibre, rayon, wool, acrylonitrile, nylon, polyester and the like.

The improved fabric may be coated, adhered or impregnated with a light sensitive, a heat sensitive or a catalyst sensitive resin and then rolled into a coil or cut into sheets as is conventional.

BRIEF DESCRIPTION OF THE DRAWINGS

FIG. 1 is a planar view of a piece of inventive knit material;

FIG. 2 is an enlargement of a section of the material of FIG. 1;

FIG. 3 is a planar view of a piece of inventive woven material;

FIG. 4 is an enlargement of a section of the material of FIG. 3;

FIG. 5 is a planar view of an alternate woven material;

FIG. 6 is an enlargement of a section of the material of FIG. 5;

FIG. 7 is a planar view of a piece of inventive nonwoven material;

FIG. 8 is a section taken along line VIII—VIII of FIG. 7;

FIG. 11 is the enlarged section of FIG. 4 impregnated with a stiffening material;

FIG. 12 is a perspective view of a roll of the improved bandage;

DESCRIPTION OF THE PREFERRED EMBODIMENTS

Figure 9:
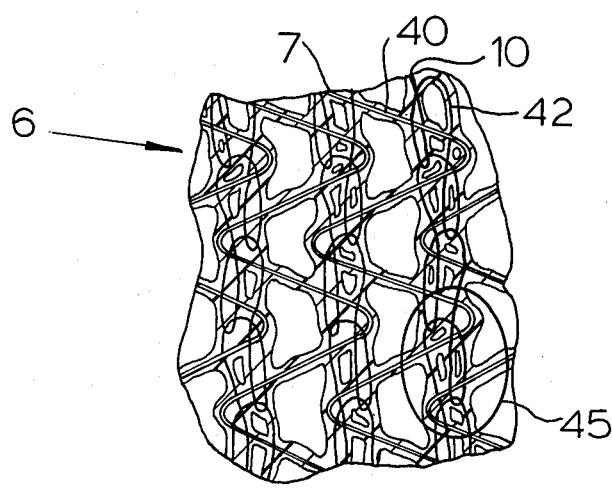
FIG. 9 is the enlarged section of FIG. 2 impregnated with a stiffening material.

Not by way of limitation, but by way of disclosing the best mode of practicing my invention and by enabling one of ordinary skilled in the art to practice my invention, there are disclosed in FIGS. 1 through 15 several alternate embodiments of my invention.

FIG. 1 is a planar view of a portion of a knitted material 5 incorporating my invention. The knitted material 5 of FIG. 1 is one form of improved two-part material knitted from a yarn made of glass fibre and a yarn made of a non-glass fibre.

FIG. 2 is an enlarged view of a region 6 of the knitted material of FIG. 1 and shows a yarn 7 formed from a fibre or fibres other than glass and a yarn 10 formed from glass fibre. The two yarns 7 and 10 are knitted together to form the improved material 5.

FIG. 3 is a planar view of a portion of a woven fabric 12 which also incorporates the principles of my invention. The woven fabric 17 is formed from a non-glass fibre yarn 15 woven together with a glass fibre yarn 17.

FIG. 4, an enlarged view of a region 18 of the material 12 of FIG. 3 shows the yarn 15 formed from fibres other than glass fibres, which is taken as the weft and woven together with the yarn 17, formed from glass fibres, which is taken as the warp of the material 12.

FIG. 5 shows an alternate woven cloth 20 which also incorporates the principles of my invention. In the woven material 20, a yarn 23 which is formed from a fibre or fibres other than glass fibres is woven together with a yarn 25 which is a yarn formed of glass fibre.

FIG. 6, an enlarged view of a region 27 of the material 20 of FIG. 5, shows the yarn 23 woven together with the yarn 25.

FIG. 7 shows yet another embodiment of my invention wherein a non-woven cloth 30 is formed out of pieces of yarn 33 formed from a fibre or fibres other than glass and pieces of yarn 35 formed from glass fibres.

FIG. 8, an enlarged sectional view of the non-woven material 30 of FIG. 7, shows the yarn 33 formed from the fibre other than glass combined with the yarn 35 formed from the glass fibre.

The compositions of tyical fabrics corresponding to the example fabrics 5,12,20,30 are shown in Table I. This invention should not be thought to be limited only to those fabrics shown in the table.

The materials disclosed in Table I may then be impregnated with a light sensitive, heat sensitive or catalytic sensitive resin of the types discussed previously to form a completed bandage.

FIG. 9 shows the region 6 of the knit cloth 5 after the cloth 5 has been impregnated with a selected resin. The non-glass yarn 7 is shown with a layer of retained resin 40. The glass yarn 10 is shown with a layer of retained resin 42.

Figure 10:
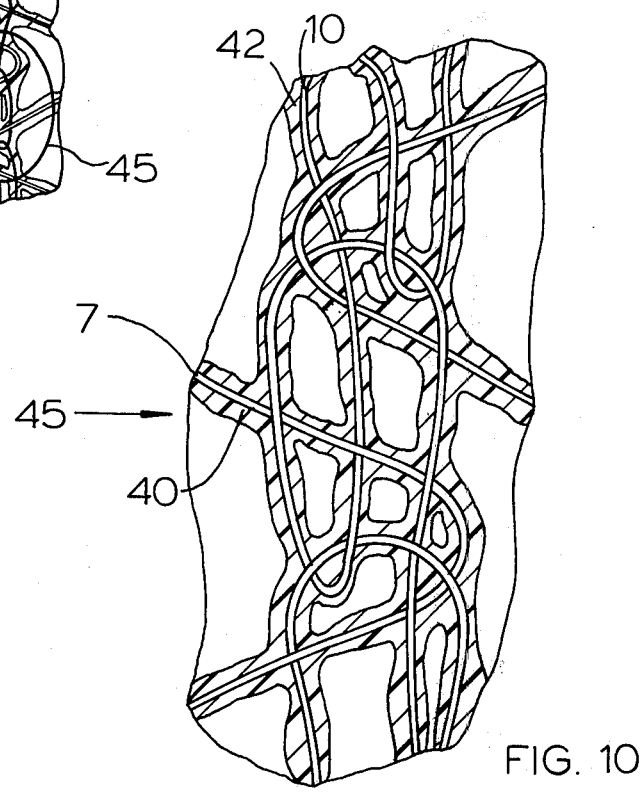
FIG. 10 is an enlargement of a section of the impregnated material of FIG. 9.

FIG. 10 is an enlarged region 45 of the region 6 of FIG. 9 and further illustrates the resin 40 retained by the non-glass fibre yarn 7 and the resin 42 retained by the glass fibre yarn 10.

FIG. 11 is a view of the enlarged region 18 of the woven material 12 after the material 12 has been impregnated with a selected resin. The yarn of glass fibres 17 is shown surrounded by a layer of solidifiable resin 46. The non-glass yarn 15 is shown with a layer of solidifiable resin 48.

TABLE I

| | Warp | | | | Woof or Weft | | | | |
| --- | --- | --- | --- | --- | --- | --- | --- | --- | --- |
| | Raw material | Count of yarn | Twist | Density | Rate of Mixing | Raw material | Count of yarn | Twist | Density | Rate of mixing |
| Knitting | Glass fibre | 202.5 TEX | 4.5 | 4 | 100% | Cotton fibre | 10 count/4 lines | 200/7 | 8 | 100% |
| | Glass fibre | 202.5 TEX | 4.5 | 4 | 100 | Cotton fibre & Glass fibre | 10 count/4 lines, 202.5 TEX | 200/7, 4.5 | 4 4 | 50 50 |
| | Glass fibre & Cotton fibre | 202.5 TEX, 10 count/4 lines | 4.5 200/7 | 2 2 | 50 50 | Cotton fibre | 10 count/4 lines | 200/7 | 8 | 100 |
| | Cotton fibre | 10 count/4 lines | 200/7 | 4 | 100 | Glass fibre | 202.5 TEX | 4.5 | 8 | 100 |
| | Glass fibre | 202.5 TEX | 4.5 | 8 | 100 | Cotton fibre | 10 count/4 lines | 200/7 | 16 | 100 |
| | Glass fibre | 202.5 TEX | 4.5 | 8 | 100 | Cotton fibre & Glass fibre | 10 count/4 lines, 202.5 TEX | 200/7, 4.5 | 8 8 | 50 50 |
| | Glass fibre & Cotton fibre | 202.5 TEX, 10 count/4 lines | 4.5 200/7 | 4 4 | 50 50 | Cotton fibre | 10 count/4 lines | 200/7 | 16 | 100 |
| | Cotton fibre | 10 count/4 lines | 200/7 | 8 | 100 | Glass fibre | 202.5 TEX | 4.5 | 10 | 100 |
| Woven cloth | Glass fibre | 202.5 TEX | 4.5 | 8 | 100 | Cotton fibre | 10 count/5 lines | 200/7 | 8 | 100 |
| | Glass fibre | 202.5 TEX | 4.5 | 8 | 100 | Cotton fibre & Glass fibre | 10 count/5 lines, 202.5 TEX | 200/7, 4.5 | 4 4 | 50 50 |
| | Glass fibre & Cotton fibre | 202.5 TEX, 10 count/5 lines | 4.5 200/7 | 4 4 | 50 50 | Cotton fibre | 20 count/5 lines | 200/7 | 8 | 100 |
| | Cotton fibre | 10 count/5 lines | 200/7 | 8 | 100 | Glass fibre | 202.5 TEX | 4.5 | 8 | 100 |

| | | Raw material | Thickness | Unit Weight | Mixing rate | Binder |
| --- | --- | --- | --- | --- | --- | --- |
| | Non-woven cloth | Glass Cotton Staple fibre | 3 mm | 150g/m$^2$ | 20 50 30 | none |
| | | Glass Polyester | 3 mm | 150g/m$^2$ | 70 80 | none |

An exemplary bandage may be made by taking a glass fibre yarn from non-alkaline glass (Japanese Spec: No. JIS.R3413) as the warp, and by taking 10 count cotton yarn, of which 5 lines have been arranged to be twisted into one having 7 twists per inch, as the weft to be set into a lengthwise knitting machine, wherein a Kroschknit is carried out to produce a knitting having a density of 4 lines lengthwise and 8 lines crosswise.

The fabric thus manufactured can be coated or impregnated with a solidifiable material having been prepared from a thermoplastic resin, which has been dissolved into toluene having a viscosity of 25,000 CPS, and then is dried. The above process of impregnation and drying is repeated until the coated fabric retains 700±10 g/m² of solidifiable material. The impregnated fabric corresponding to the impregnated fabrics of FIGS. 9-11 may then be cut into unit pieces having a length of 2 m and a width of 10 cm. The cut pieces can then be rolled into a coil.

When an impregnated bandage is rolled into a coil such as the coil 62 of FIG. 12, a polyethylene sheet (0.05 mm thick) 65 is sandwiched between each layer 67 of the roll 62 to prevent the each layer 67 from sticking to the adjacent layer when the roll 62 is unwound to be used.

This invention has the further advantage that the strength, ventilability, flexibility, etc. of the bandage may be suitably varied by adjusting the ratio of glass fibre and other fibre, fibre size, density of twisting or method of weaving or knitting.

An especially suitable material for a stiff supporting bandage such as the bandage 12 according to this invention, is a cloth with a warp having 20-70% by weight of glass fibre and weft of a natural fibre such as cotton, flax and wool, or of staple fibre.

Stiff supporting bandages such as the bandage 62 may be formed in rolls or as stacks of pre-cut bandages.

The stiff supporting bandage 62 consisting of a two-part fabric as discussed previously can incorporate as a slidifiable material a solidifiable thermoplastic resin. The thermoplastic resin can be used to impregnate the two-part material according to this invention. To soften the bandage, it may be immersed into water at about 70°-80° C. for about 3-5 minutes. Then, having taken it out of the hot water and having removed any excess water therefrom, the bandage 62 may be applied to the damaged member.

Figure 13:
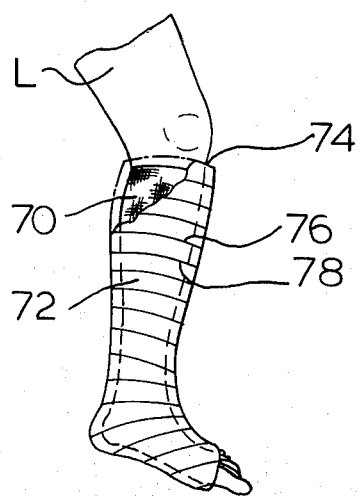
FIG. 13 is a view of a leg cast, partly broken away, formed from the improved bandage.

As shown in FIG. 13, an under-wrapping bandage 70 of cotton or sponge having a cushioning effect may first be applied over the injured member L. A supporting bandage 72 may be wound in half lap for 3 to 4 layers about the damaged portion of the limb L, over the under-wrapping layer 70. The supporting bandage 72 may then be manually compressed along the edge line 74 and the overlapping edges 76, 78 to improve adherence between layers. If necessary, the shape of the bandage 72 may be adjusted so that the edge line 74 does not contact the damaged region. The bandage may be left for about 7 to 8 minutes to solidify and become adequately rigid and strong.

If desired, the solidifying rate of the bandage 72 may be accelerated by applying a cool towel or a cool draft thereto. If the solidifiable material is a thermoplastic material, the solidified bandage 72 may be reheated by a hot towel or by means of a dryer to soften it again locally or as a whole. The softened bandage 72 may further be altered in shape or reinforced by applying another bandage in superposition one the softened bandage.

Figure 14:
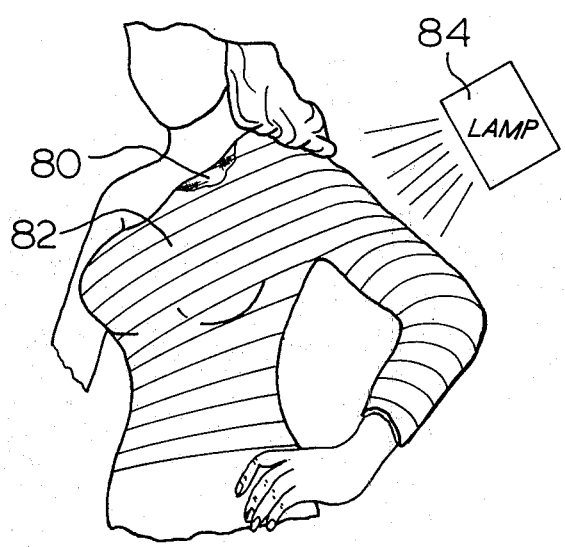
FIG. 14 is a perspective view of a body cast being irradiated with light of a selected frequency.

A stiff supporting bandage according to this invention, in which a photo-sensitive resin has been applied to the basic fabric, should be packed in a package impermeable to light. The packaging film may be opened just before the bandage is to be applied to the damaged portion. As shown in FIG. 14, the damaged region should have previously been covered by an under-wound material 80 having a cushioning effect. A stiff supporting bandage 82 may then be wound in half lap for 3-4 layers. By radiating the bandage 82 with an ultraviolet ray lamp 84, which will emit a ray of 3,900 Å, for about 8-10 minutes, the photosensitive material can be adequately hardened.

In addition to using the solidifiable bandages according to this invention for rectifying or supporting damaged sprains or deformations in human or animal bodies, they may also be utilized to create art objects, as clay is used for modelling of human bodies, for creating architectural and civil engineering models and for the reinforcement of such objects.

Figure 15:
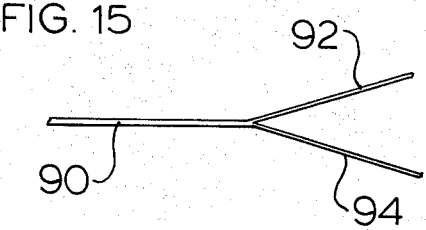
FIG. 15 is a schematic view of a compound yarn being formed from glass and non-glass fibres.

FIG. 15 shows a compound yarn 90, suitable for use in an improved bandage such as the bandage 62, being formed of glass fibres 92 and non-glass fibres 94.

In summary, the stiff supporting bandage according to this invention is uniquely effective due to the use of an improved fabric prepared by selectively combining the glass firbre and one or more other fibres; and it may be summarized as follows:

(A) The glass fibre included in the improved fabric not only makes it easier to develop the rigidity thereof but also, by combining the glass fibre with another fibre, the fabric adheres better to the solidifiable material in contrast to a fabric formed from the glass fibre alone. That is to say, the property inherent to the glass fibre is utilized much more effectively than in the prior art.

Consequently, the amount of bandage may be decreased by ⅓ to ½ of the amount that any conventional bandage would use for a given injury. There will thus be a considerable reduction in the application time as well as a reduced burden on the patient due to the lesser amount of bandage material being needed.

(B) There is a difference in the adherence of the glass fibre and other fibres to the solidifiable material. By suitably selecting the ratio between the amounts of both kinds or fibres, any desired amount of such material may be adhered on the basic fabric. Additionally, bandage quality may be stabilized and the manufacture of the bandage may be simplified.

(C) When a conventional bandage utilizing only glass fibre is applied to the damaged portion of a patient, pain is often experienced due to the pricking of the pointed ends of the glass fibre against adjacent body areas. By adjusting the amount of the solidifiable material to be adhered to the fabric, the edges of the bandage may suitably be rounded by the material, whereby the patient can be relieved from such trouble, resulting in a more comfortable bandage.

While various modifications and changes might be suggested by those skilled in the art, it will be understood that I wish to include within the claims of the patent warrented hereon all such modifications and changes as reasonably come within my contribution to the art.

I claim as my invention:

1. A fabric adapted to be impregnated with a selected, hardenable, stiffening material thereby forming an initially flexible bandage that can be coverted to a light weight, strong, rigid bandage by curing the stiffening material, said fabric comprising:

an amount of a first fiber and an amount of a second fiber combined together, said first fiber is formed of glass fibers, said second fiber is a fiber selected from a class containing cotton, flax, staple fiber, wool, acrylic resin, nylon, rayon and polyester, said amount of said glass fiber has a weight selected from a range of 20% to 70% of the total weight of said fabric, said first and second fibers are formed as first and second yarns and are woven together, said second yarn is a compound yarn formed of said second fiber combined with a third fiber selected from said class.

* * * * *